United States Patent [19]

Brizzard et al.

[11] Patent Number: 5,731,425
[45] Date of Patent: Mar. 24, 1998

[54] POLYPEPTIDE SURFACE MARKER FOR CELLS

[75] Inventors: Billy L. Brizzard, New Haven; Darlene W. Bianca, Westbrook; Richard G. Chubet, Middletown; Douglas L. Vizard, Cheshire, all of Conn.; Thomas Patrick Hopp, San Diego, Calif.

[73] Assignee: Eastman Kodak Company, Rochester, N.Y.

[21] Appl. No.: 330,638

[22] Filed: Oct. 28, 1994

[51] Int. Cl.$^6$ .............. C07H 21/04; C12P 21/02; C12N 15/11; C12N 15/85

[52] U.S. Cl. .............. 536/23.1; 435/69.1; 435/320.1; 536/24.1

[58] Field of Search .............. 435/320.1, 69.1, 435/69.7, 69.8, 252.3, 254.11; 536/23.1, 23.4, 23.5, 24.1; 530/350; 930/10, 300; 935/22, 47, 48, 66

[56] References Cited

U.S. PATENT DOCUMENTS

| | | | |
|---|---|---|---|
| 4,650,756 | 3/1987 | Old et al. | 435/7.23 |
| 4,703,004 | 10/1987 | Hopp et al. | 435/69.7 |
| 4,782,137 | 11/1988 | Hopp et al. | 530/328 |
| 4,810,632 | 3/1989 | McMillan | 435/7.21 |
| 4,851,341 | 7/1989 | Hopp et al. | 435/69.7 |
| 4,978,621 | 12/1990 | Ardeshir et al. | 435/252.3 |
| 5,011,912 | 4/1991 | Hopp et al. | 530/387.9 |
| 5,124,251 | 6/1992 | Lanier et al. | 435/7.21 |
| 5,185,438 | 2/1993 | Lemischka | 536/23.2 |
| 5,242,822 | 9/1993 | Marullo et al. | 435/252.3 |
| 5,270,458 | 12/1993 | Lemischka | 536/23.5 |
| 5,336,597 | 8/1994 | McMillan | 435/7.2 |

OTHER PUBLICATIONS

Bianca et al. "Use of the Flag Epitope to Expression Expression & Function of a Synthetic Gene . . . " Mol. Biol. Cell. 4(Suppl) 192A #1121 1993.

Kriegler, M., Gene Transfer and Expression a Laboratory Manual, W.H. Freeman and Company, New York (1990).

Wigler et al., Cell, vol. 11, p. 223 (1977).

Southern et al., J. Mol Appl. Gen. vol. 1, p. 327 (1982).

Padmanabhan, et al., Methods in Enzymology, vol. 218, pp. 637–651 (1993).

*Primary Examiner*—David Guzo
*Assistant Examiner*—Nancy J. Degen

[57] ABSTRACT

This invention discloses a gene for the identification of cells comprising a selection leader segment, a cell marker segment and a transmembrane segment. The gene can be used to identify cells transfected with the gene by the steps of: inserting the gene having a selection leader segment, a cell marker segment and a transmembrane segment into the DNA or RNA of a cell, allowing the cell to express the gene, and detecting the expressed cell marker segment of the gene.

12 Claims, 3 Drawing Sheets

A. DNA sequence of the 204 base coding region of the FLAG-SG SEQ ID NO:1:

5'-ATGTCTGCACTTCTGATCCTAGCTCTTGTTGGAGCTGCAGTTGCTGACTACAAAGAC
GATGACGACAAGACCCCCGAGAACACCAGGAGGTTCCCGTCAGCAGTGCCCCTAGTG
GCCCCCTAACTGAGATCATCATTGTGACTGGAGTGCTGCTGGCCCTCTTAGTGAGCATC
CTGGGTGCTTTCATGCTGTACCGGCAGACGC-3'

FIG. 1A

B. Amino acid sequence of the FLAG-SG    SEQ ID NO:2:

Preprotrypsin                    Flag
N-MSALLILALVGAAVA/DYKDDDDK/

Glycosylated spacer
/TPENTSEVPASSAPSGPLTEI/

Transmembrane segment        /Cytoplasmic anchor
/IIVTGVLLALLVSILGAFMLY/RRR-C

FIG. 1B

FSG-1: CTATGTCGACTTTCTGTCACCATGTCTGCACTTCTGATCCTAGCTCTTGTTG (SEQ ID NO:3)
FSG-2: CGTCATCGTCTTGTAGTCAGCAACTGCAGCTCCAACAAGAGC (SEQ ID NO:4)
FSG-3: ACGATGACGACAAGACCCCGAGAACACCAG (SEQ ID NO:5)
FSG-4: GGAACCTCGCTGGTGTC (SEQ ID NO:6)
FSG-5: CGAGGTTCCCGCCTAGCAGTGCCCCTAGTGCCCCCTAACTGAGA (SEQ ID NO:7)
FSG-6: CGAGCAGCACTCCAGTCACAATGATGATCTCAGTTAGG (SEQ ID NO:8)
FSG-7: GCTGCTGGCCTCTTAGTGAGCATCCTGGGTGCTTC (SEQ ID NO:9)
FSG-8: CTAAGAATTCATTAGCGTCTGCGGTACAGCATGAAAGCACC (SEQ ID NO:10)

SEQUENCE LISTING ( 1 ) GENERAL INFORMATION:

( i i i ) NUMBER OF SEQUENCES:10

( 2 ) INFORMATION FOR SEQ ID NO:1:

( i ) SEQUENCE CHARACTERISTICS:
        ( A ) LENGTH: 204 base pairs
        ( B ) TYPE: Nucleic Acid
        ( C ) STRANDEDNESS: DOUBLE ( D ) TOPOLOGY: Linear ( i i ) MOLECULE TYPE: SYNTHETIC GENE ( i i i ) HYPOTHETICAL: NO ( i v ) ANTI-SENSE: NO ( v i ) ORIGINAL SOURCE: SYNTHETICALLY PREPARED ( v i i ) IMMEDIATE SOURCE: SYNTHETICALLY PREPARED ( i x ) FEATURE: SECRETION LEADER SEQUENCE
LOCATION: 1-45
FEATURE: CELL MARKER SEGMENT
LOCATION: 46-69
FEATURE: SPACER SEGMENT
LOCATION: 70-132
FEATURE: TRANSMEMBRANE SEGMENT
LOCATION: 133-195
FEATURE: ANCHOR SEGMENT
LOCATION: 196-204

( x ) PUBLICATION INFORMATION: NONE ( x i ) SEQUENCE DESCRIPTION: SEQ ID NO: 1:

| ATGTCTGCAC | TTCTGATCCT | AGCTCTTGTT | GGAGCTGCAG | TTGCTGACTA | 50 |
| CAAAGACGAT | GACGACAAGA | CCCCCGAGAA | CACCAGCGAG | GTTCCCGCTA | 100 |
| GCAGTGCCCC | TAGTGGCCCC | CTAACTGAGA | TCATCATTGT | GACTGGAGTG | 150 |
| CTGCTGGCCC | TCTTAGTGAG | CATCCTGGGT | GCTTTCATGC | TGTACCGCAG | 200 |
| ACGC | | | | | 204 |

( 2 ) INFORMATION FOR SEQ ID NO:2:

( i ) SEQUENCE CHARACTERISTICS:
( A ) LENGTH: 68 AMINO ACID RESIDUES
( B ) TYPE: AMINO ACID
( D ) TOPOLOGY: LINEAR ( i i ) MOLECULE TYPE: PROTEIN ( i i i ) HYPOTHETICAL: NO ( i v ) ANTI-SENSE: NO ( v i ) ORIGINAL SOURCE: SYNTHETICALLY PREPARED ( v i i ) IMMEDIATE SOURCE: SYNTHETICALLY PREPARED ( i x ) FEATURE: SECRETION SEQUENCE
LOCATION: 1-15
FEATURE: CELL MARKER SEGMENT
LOCATION: 16-23
FEATURE: SPACER SEGMENT
LOCATION: 24-44
FEATURE: TRANSMEMBRANE SEGMENT
LOCATION: 45-65
FEATURE: ANCHOR SEGMENT
LOCATION: 66-68

( x ) PUBLICATION INFORMATION: NONE ( x i ) SEQUENCE DESCRIPTION: SEQ ID NO:2:

```
Met Ser Ala Leu Leu Ile Leu Ala Leu Val Gly Ala Ala Val
                 5                  10
Ala Asp Tyr Lys Asp Asp Asp Lys Thr Pro Glu Asn Thr
 15              20                  25
Ser Glu Val Pro Ala Ser Ser Ala Pro Ser Gly Pro Leu Thr
         30              35              40
Glu Ile Ile Ile Val Thr Gly Val Leu Leu Ala Leu Leu Val
```

```
                    45                  50                     55
Ser  Ile  Leu  Gly  Ala  Phe  Met  Leu  Tyr  Arg  Arg  Arg
                 60                      65
```

(2) INFORMATION FOR SEQ ID NO:3:

(i) SEQUENCE CHARACTERISTICS:
        (A) LENGTH: 52 BASES
        (B) TYPE: NUCLEIC ACID
        (C) STRANDEDNESS: SINGLE
        (D) TOPOLOGY: LINEAR     (ii) MOLECULE TYPE: SYNTHETIC OLIGONUCLEOTIDE     (iii) HYPOTHETICAL: NO     (iv) ANTI-SENSE: NO     (vi) ORIGINAL SOURCE: SYNTHETICALLY PREPARED
        (vii) IMMEDIATE SOURCE: SYNTHETICALLY PREPARED     (x) PUBLICATION INFORMATION: NONE     (xi) SEQUENCE DESCRIPTION: SEQ ID NO:3:

```
CTATGTCGAC TTTCTGTCAC CATGTCTGCA CTTCTGATCC        40
TAGCTCTTGT TG                                      52
```

(2) INFORMATION FOR SEQ ID NO:4:

(i) SEQUENCE CHARACTERISTICS:
        (A) LENGTH: 43 BASES
        (B) TYPE: NUCLEIC ACID
        (C) STRANDEDNESS: SINGLE
        (D) TOPOLOGY: LINEAR     (ii) MOLECULE TYPE: SYNTHETIC OLIGONUCLEOTIDE     (iii) HYPOTHETICAL: NO     (iv) ANTI-SENSE: YES     (vi) ORIGINAL SOURCE: SYNTHETICALLY PREPARED     (vii) IMMEDIATE SOURCE: SYNTHETICALLY PREPARED     (x) PUBLICATION INFORMATION: NONE     (xi) SEQUENCE DESCRIPTION: SEQ ID NO:4:

```
CGTCATCGTC TTTGTAGTCA GCAACTGCAG CTCCAACAAG AGC    43
```

(2) INFORMATION FOR SEQ ID NO:5:

(i) SEQUENCE CHARACTERISTICS:
        (A) LENGTH: 31 BASES
        (B) TYPE: NUCLEIC ACID
        (C) STRANDEDNESS: SINGLE
        (D) TOPOLOGY: LINEAR     (ii) MOLECULE TYPE: SYNTHETIC OLIGONUCLEOTIDE     (iii) HYPOTHETICAL: NO     (iv) ANTI-SENSE: NO     (vi) ORIGINAL SOURCE: SYNTHETICALLY PREPARED     (vii) IMMEDIATE SOURCE: SYNTHETICALLY PREPARED     (x) PUBLICATION INFORMATION: NONE     (xi) SEQUENCE DESCRIPTION: SEQ ID NO:5:

```
ACGATGACGA CAAGACCCCC GAGAACACCA G                 31
```

( 2 ) INFORMATION FOR SEQ ID NO:6:

( i ) SEQUENCE CHARACTERISTICS:
        ( A ) LENGTH: 18 BASES
        ( B ) TYPE: NUCLEIC ACID
        ( C ) STRANDEDNESS: SINGLE
        ( D ) TOPOLOGY: LINEAR     ( i i ) MOLECULE TYPE: SYNTHETIC OLIGONUCLEOTIDE     ( i i i ) HYPOTHETICAL: NO     ( i v ) ANTI-SENSE: YES     ( v i ) ORIGINAL SOURCE: SYNTHETICALLY PREPARED     ( v i i ) IMMEDIATE SOURCE: SYNTHETICALLY PREPARED     ( x ) PUBLICATION INFORMATION: NONE     ( x i ) SEQUENCE DESCRIPTION: SEQ ID NO: 6:

GGAACCTCGC TGGTGTTC     18

( 2 ) INFORMATION FOR SEQ ID NO:7:

( i ) SEQUENCE CHARACTERISTICS:
        ( A ) LENGTH: 44 BASES
        ( B ) TYPE: NUCLEIC ACID
        ( C ) STRANDEDNESS: SINGLE
        ( D ) TOPOLOGY: LINEAR     ( i i ) MOLECULE TYPE: SYNTHETIC OLIGONUCLEOTIDE     ( i i i ) HYPOTHETICAL: NO     ( i v ) ANTI-SENSE: NO     ( v i ) ORIGINAL SOURCE: SYNTHETICALLY PREPARED     ( v i i ) IMMEDIATE SOURCE: SYNTHETICALLY PREPARED     ( x ) PUBLICATION INFORMATION: NONE     ( x i ) SEQUENCE DESCRIPTION: SEQ ID NO:7:

CGAGGTTCCC GCTAGCAGTG CCCCTAGTGG CCCCCTAACT GAGA     44

( 2 ) INFORMATION FOR SEQ ID NO:8:

( i ) SEQUENCE CHARACTERISTICS:
        ( A ) LENGTH: 38 BASES
        ( B ) TYPE: NUCLEIC ACID
        ( C ) STRANDEDNESS: SINGLE
        ( D ) TOPOLOGY: LINEAR     ( i i ) MOLECULE TYPE: SYNTHETIC OLIGONUCLEOTIDE     ( i i i ) HYPOTHETICAL: NO     ( i v ) ANTI-SENSE: YES     ( v i ) ORIGINAL SOURCE: SYNTHETICALLY PREPARED     ( v i i ) IMMEDIATE SOURCE: SYNTHETICALLY PREPARED     ( x ) PUBLICATION INFORMATION: NONE     ( x i ) SEQUENCE DESCRIPTION: SEQ ID NO:8:

CCAGCAGCAC TCCAGTCACA ATGATGATCT CAGTTAGG     38

( 2 ) INFORMATION FOR SEQ ID NO:9:

( i ) SEQUENCE CHARACTERISTICS:

(A) LENGTH: 37 BASES
(B) TYPE: NUCLEIC ACID
(C) STRANDEDNESS: SINGLE
(D) TOPOLOGY: LINEAR (i i) MOLECULE TYPE: SYNTHETIC OLIGONUCLEOTIDE (i i i) HYPOTHETICAL: NO (i v) ANTI-SENSE: NO (v i) ORIGINAL SOURCE: SYNTHETICALLY PREPARED (v i i) IMMEDIATE SOURCE: SYNTHETICALLY PREPARED (x) PUBLICATION INFORMATION: NONE (x i) SEQUENCE DESCRIPTION: SEQ ID NO:9:

GCTGCTGGCC CTCTTAGTGA GCATCCTGGG TGCTTTC 37

(2) INFORMATION FOR SEQ ID NO:10:

(i) SEQUENCE CHARACTERISTICS:
(A) LENGTH: 41 BASES
(B) TYPE: NUCLEIC ACID
(C) STRANDEDNESS: SINGLE
(D) TOPOLOGY: LINEAR (i i) MOLECULE TYPE: SYNTHETIC OLIGONUCLEOTIDE (i i i) HYPOTHETICAL: NO (i v) ANTI-SENSE: YES (v i) ORIGINAL SOURCE: SYNTHETICALLY PREPARED (v i i) IMMEDIATE SOURCE: SYNTHETICALLY PREPARED (x) PUBLICATION INFORMATION: NONE (x i) SEQUENCE DESCRIPTION: SEQ ID NO:10:

CTAAGAATTC ATTAGCGTCT GCGGTACAGC ATGAAAGCACC 41

POLYPEPTIDE SURFACE MARKER FOR CELLS

TECHNICAL FIELD

The present invention relates to a synthetic gene which encodes for a polypeptide surface marker for cells which can be used to identify cells which have been transfected with the synthetic gene sequence. More specifically, this invention relates to a synthetic gene which encodes for a polypeptide surface marker for cells which through the use of an affinity technique can be used to identify cells which have been transfected with the synthetic gene.

BACKGROUND OF THE INVENTION

Recombinant DNA techniques in which transfection vectors are inserted into cells are used to express genes for experimental study, gene replacement and the production of commercial products, such as, proteins, enzymes, and hormones. It is often desirable to have a selectable marker for identification of cells into which the transfection vector has been inserted. Presently, most DNA transfection vectors have as part of their gene code dominant selectable markers which provide the transfected cells, which are the cells into which the transfection vectors have been inserted, resistance to drugs or nutrient-depleted growth medium so that the transfected cells can be selected using the drug or the absence of the nutrient in the growth medium to kill the cells that do not have the transfection vector. Examples of these DNA transfection vectors are reviewed in Kriegler, M., *Gene Transfer and Expression a Laboratory Manual*, W. H. Freeman and Company, New York (1990).

Most methods of selecting transfected cells which require the use of drugs or nutrient-depleted growth mediums to select the cells are laborious and time consuming. For example, Wigler et al., *Cell*, Vol. 11, pg. 223 (1977) describe a method in which a transfection vector having the herpes virus thymidine kinase (TK) gene is inserted into cultured mouse cells which do not originally have the TK gene. The TK gene confers resistance to the drug aminopterin. In addition to requiring a special growth medium (HAT medium), the drug aminopterin is required to select the transfected cells. This selection method takes several days.

Another example of a commonly utilized selectable marker in a transfection vector is the aph gene which encodes resistance to the drug G418™ supplied by Life Technologies, Inc. This gene and the method of its use to select transfected cells is described in Southern, P. et al., *J. Mol Appl. Gen.* Vol. 1, pg. 327 (1982). To select the transfected cells with the aph gene a titration requiring several days must be performed on the cell sample prior to the introduction of the transfection vector, and after the introduction of the transfection vector to the cell sample the concentration level of G418™ must be maintained at the maximum tolerable drug level for several days to kill the nontransfected cells. This long process can be deleterious to the desired transfected cells.

It is commonplace to use toxic drugs as the means of selecting transfected cells; however, the toxic drugs can be toxic to the transfected cells or they can retard the Growth of the transfected cells.

Padmanabhan, et al., *Methods in Enzymology*, Vol. 218, pp. 637–651 (1993) describe genes for naturally-occurring cell surface markers. Two examples of the naturally occurring cell surface markers are the vesicular stomatitis virus glycoprotein (VSV-G) and the multiple drug resistance marker (mdr). Transfected cells which express the gene for naturally-occurring cell surface markers are identified using antibodies which are specific to the cell surface marker. Genes expressing naturally-occurring cell surface markers are deficient, because they have inherent biological properties which may interfere with normal cell function. Also, most naturally-occurring cell markers are large proteins whose genes take up more space in a tranfection vector, are harder to work with, are prone to having unwanted restriction enzyme sites and are more of a protein synthesis burden on the transfected cell.

There is therefore presently a need in the art for genes which express selectable markers which can be used in transfection vectors for the identification and selection of transfected cells, which are not naturally occurring markers, do not require laborious and time consuming techniques, and do not use toxic drugs to identify the transfected cells.

SUMMARY OF THE INVENTION

The present invention provides a synthetic gene for the identification or selection of cells comprising: a secretion leader segment, a cell marker segment and a transmembrane segment. The present invention also provides the method of selecting cells comprising the steps of: inserting the synthetic gene into a sample of cells, said synthetic gene comprises a secretion leader segment, a cell marker segment and a transmembrane segment; allowing said sample of cells to express said synthetic gene; and using an affinity technique to identify the expressed synthetic gene.

This invention represents a significant improvement over conventional genes and methods which are useful for the identification of the cells transfected with a gene, because the synthetic gene of this invention and the polypeptide surface marker encoded by the synthetic gene are not known to occur in nature; therefore, they possess no inherent biological properties which may interfere with the biological activities of the transfected cells. This allows for the use of the synthetic gene in most cells. Additionally, the methods of identification do not require the use of toxic drugs and they are typically less laborious and less time consuming than other conventional methods.

DETAILED DESCRIPTION OF THE INVENTION

The term "synthetic" when used herein to describe a gene or a segment of a gene means a piece of DNA or RNA which is produced in the laboratory by known techniques of molecular biology by chemical linkage of the deoxyribonucleotides or ribonucleotides.

The term "segment" when used herein refers to a section of the entire nucleotide sequence which makes up the synthetic gene.

The term "transfection vector" as used herein unless otherwise specified is any piece of DNA or RNA which can be inserted into a cell's DNA or RNA.

The term "identify" or "identification" used herein in reference to cells transfected with the synthetic gene of this invention, unless otherwise indicated means to mark, to purify, to enrich, to select, to isolate, or to separate. Identification can be by a single or multiple steps.

The term "gene" refers to a sequence of deoxyribonucleic acids or ribonucleic acids that have some effect on a cell.

For all the nucleotide and amino acid sequences disclosed and described in here, it is understood that equivalent nucleotides and amino acids can be substituted into the sequences without affecting the function of the sequences. Additionally, such substitution may be necessary to use the disclosed sequences in cells which differ from those described in the specific embodiments herein. Such substitution is within the ability of a person of ordinary skill in the art.

The synthetic gene of this invention can be used for the identification of cells. The synthetic gene can be used in all cells, preferably nucleated cells, more preferably animal cells such as insect, arian, reptile and most preferably mammalian. The synthetic gene is preferably used for the identification and selection of cells transfected with the synthetic gene for many purposes, including experimental study, commercial production, and gene replacement.

The present invention provides a synthetic gene for the identification of cells, the synthetic gene comprises a secretion leader segment, a cell marker segment and a transmembrane segment. Preferably the synthetic gene further consists of a spacer segment or an anchor segment. Most preferably the synthetic gene consists of, in order, a secretion leader segment, a cell marker segment, a spacer segment, a transmembrane segment and an anchor segment.

Figure 1A:
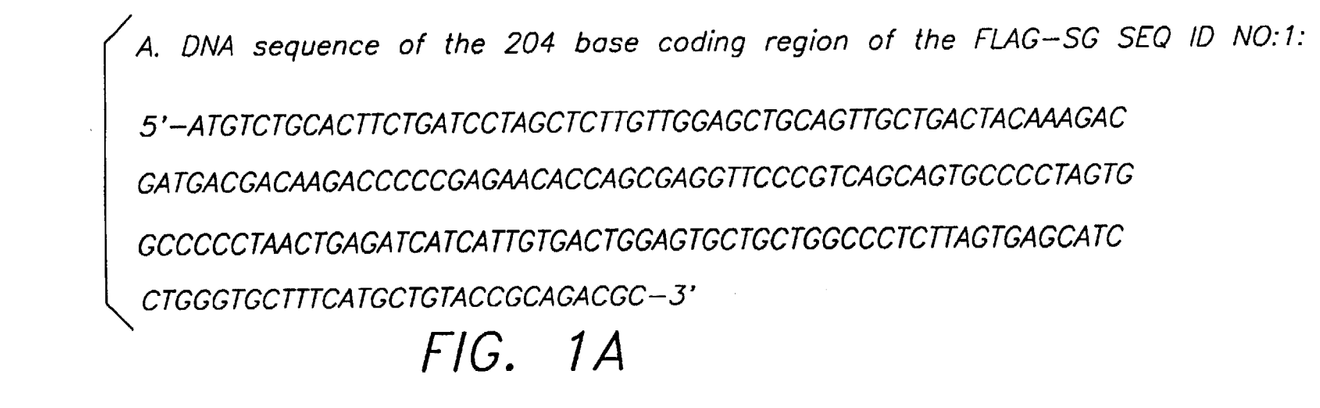
FIG. 1A shows the DNA sequence of the 204 base coding region of the synthetic gene (SEQ ID NO:1).

The secretion leader segment otherwise known in the art as a signal sequence segment directs the insertion of the expressed synthetic gene product into the cell membrane. Many secretion leader segments are known in the art and can be used in the synthetic gene of this invention. Examples of secretion leader segments include the LDL receptor, human serum albumin, mouse immunoglobulin, chicken lysozyme and others disclosed in von Heijne, G., *J. Mol. Biol.*, Vol 184, pp. 99–105 (1985), incorporated herein by reference. Preferably the first codon of the secretion leader segment is the initiator methionine. The most preferred secretion leader segment consists of nucleotides 1 through 45 of SEQ ID NO:1; SEQ ID NO:1 is also shown in FIG. 1A. Nucleotides, 1 through 45 of SEQ ID NO:1 encode the preprotrypsin secretion leader segment.

The cell marker segment of the synthetic gene encodes a polypeptide surface marker. The polypeptide surface marker is expressed by the cell into which the synthetic gene is transfected. The cell marker segment and the polypeptide surface marker which it encodes are preferably unnatural, that is, not naturally occurring. It is preferable to place the cell marker segment after, more preferably immediately after the secretion leader segment in the synthetic gene to increase the likelihood that the cell will secrete the polypeptide surface marker through the cell membrane. It is also preferred that the cell marker segment encode for a polypeptide surface marker which is useful in an affinity selection technique. Examples of affinity selection techniques are known in the art and are discussed in more detail below. The preferred polypeptide surface markers are short, preferably consisting of less than 50 amino acids. Additionally it is preferred that the polypeptide surface markers are antigenic, therefore, antibodies specific to the polypeptide surface markers can be employed for identification of the cells transfected with the synthetic gene of this invention. Examples of synthetic cell marker segments which may be used in the synthetic gene of this invention include segments which encode the Histidine Sequence and FLAG®. The Histidine Sequence is disclosed and described in Hochuli, et al., *J. of Chromat.*, Vol. 411, pp. 177–184 (1987), incorporated herein by reference. FLAG® is a registered trade mark of Immunology Ventures and is commercially available form the Eastman Kodak Co.

A preferred cell marker segment of the present invention is one which expresses a polypeptide surface marker comprising both hydrophilic and aromatic amino acids and including the sequence Asp-Tyr-Lys (amino acid residues 16–17 of SEQ ID NO:2) or an equivalent sequence. Also preferred are cell marker segments encoding and expressing polypeptide surface markers comprising a plurality of amino acids selected from the group consisting of Arg, Asp, Glu, Lys, Tyr, Phe, His and Trp. The most preferred cell marker segment is the FLAG® polypeptide. The preferred form of FLAG® consists of an eight amino acid sequence: Asp-Tyr-Lys-Asp-Asp-Asp-Asp-Lys (amino acid residues 16–23 of SEQ ID NO:2), as disclosed and described in U.S. Pat No. 5,011,912, incorporated herein by reference. Other patents disclosing FLAG® and the use of FLAG® are U.S. Pat. Nos. 4,703,004; 4,782,137; and 4,851,341; each incorporated herein by reference. Nucleotides 46 through 69 of SEQ ID NO:1 and as shown in FIG. 1A encode the FLAG sequence.

To be useful as a polypeptide surface marker, the polypeptide surface marker must remain attached to the cell until the cells expressing the polypeptide surface marker can be identified or selected. The transmembrane segment of the synthetic gene is useful for anchoring the expressed polypeptide surface marker to the membrane. Examples of useful transmembrane segments include the transmembrane segments of the cell surface receptors disclosed and described in Padmanabhan, et al. *Methods in Enzymology*, Vol. 218, pp. 637–651 (1993) and in U.S. Pat. No. 5,270, 458. Both of these disclosures are incorporated herein by reference. The preferred transmembrane segments encode integral transmembrane polypeptides. Also the preferred transmembrane segment is a synthetic consensus gene sequence, and therefore does not express a transmembrane polypeptide which corresponds exactly to any naturally occurring transmembrane polypeptide. A synthetic consensus sequence is preferred to avoid any unwanted inherent biological properties so that the transmembrane polypeptide encoded by the synthetic gene will not interfere with normal cell function. The most preferred transmembrane segment consists of nucleotides 133 through 195 of SEQ ID NO:1 and as shown in FIG. 1A.

When the transmembrane polypeptide cannot effectively hold the polypeptide surface marker to the cell, or to be sure that the transmembrane polypeptide holds the polypeptide surface marker to the cell, the synthetic gene preferably consists of an anchor segment which encodes an anchor polypeptide. The anchor segment is preferably present in the synthetic gene after, more preferably immediately after the transmembrane segment. The anchor polypeptide, preferably a cytoplasmic anchor polypeptide, stops the transfer of the entire expressed product of the synthetic gene through the cell membrane and therefore holds the polypeptide surface marker to the cell, but outside the cell membrane where it can be detected by affinity techniques which can be used to identify and select cells transfected with the synthetic gene.

The anchor segment is an optional component of the synthetic gene of this invention. It may not be necessary when a transmembrane segment encoding an integral transmembrane polypeptide is used; however, it is preferable to include the anchor segment in the synthetic gene. The anchor segment and the anchor polypeptide can be naturally occurring or not naturally occurring. Examples of anchor polypeptides that can be used in this invention include those found at the cytoplasmic terminus of membrane immunoglobulins. Yamawaki-Kataoka, Y. et al., *Proc. Natl. Acad. Sci.*, Vol. 79, pp. 2623–2627 (1982). The most preferred cytoplasmic anchor segment encodes three arginine residues. The most preferred cytoplasmic anchor segment consists of nucleotides 196 through 204 of SEQ ID NO:1 and as shown in FIG. 1A.

Another optional, but preferred segment of the synthetic gene is a spacer segment. The spacer segment of the synthetic gene encodes a spacer polypeptide which when the synthetic gene is expressed by the cell can be used to hold the polypeptide surface marker for the cell away from the cell membrane to increase the likelihood that the polypeptide surface marker will be identified by the chosen affinity technique. The spacer polypeptide is optional when the polypeptide surface marker, alone or in combination with the transmembrane polypeptide, is held sufficiently away from the cell membrane so that the polypeptide surface marker can be detected by the chosen affinity technique or if the chosen affinity technique does not require that the polypeptide surface marker be held away from the cell membrane in order to detect it.

When a spacer segment is present in the synthetic gene, it is preferably located between the surface marker segment and the transmembrane segment. The preferred spacer segments express glycosylated spacer polypeptides. The glycosylated spacer polypeptides can be either naturally occurring or synthetic. For example, one naturally occurring glycosylated spacer polypeptide includes the human LDL receptor described in Yamamoto et al, *Cell*, Vol 39, pp. 27–38, (1984). Other examples include the insulin receptor, described in Rosen, O. M., *Science*, Vol. 237, pp. 1452–1458 (1987); and the EGF precursor described in Gray, A. et al., *Nature*, Vol. 303, pp. 722–725 (1983). All three references are incorporated herein by reference. The most preferred spacer polypeptides and segments are synthetic peptides and segments which are similar to the naturally occurring glycosylated spacer polypeptides and spacer segments found in many cell surface receptors, and which possess features thought to be important in such polypeptides and segments.

It is preferred that the amino acid sequence of the spacer polypeptide includes multiple glycosylation sites. The glycosylation sites help to extend the spacer polypeptide and the polypeptide surface marker away from the cell surface. The spacer polypeptide can contain any combination of consensus sites for N-Linked, O-Linked, and glycosaminoglycan type carbohydrate moieties; most preferably the expressed spacer segment will possess all three types of consensus sites.

The spacer polypeptide should be large enough to move the polypeptide surface marker away from the cell membrane and out of the glycocalyx, if present on the transfected cell's membrane. The glycocalyx might otherwise interfere with affinity selection. It is preferred that the amino acid sequence of the spacer polypeptide possesses a net charge that is of the same sign as the net charge of the surface of the membrane of the cell into which the synthetic gene having the spacer segment was transfected. The similarity in the net charges of the spacer polypeptide and the surface of the cell membrane helps to repel the spacer polypeptide away from the cell membrane. For example if the surface of the mammalian cell that is transfected with the synthetic gene has a net negative charge, it is preferred that the spacer polypeptide possess a net negative charge.

The most preferred spacer segment is glycosylated and not naturally occurring and is represented by nucleotides 70 through 132 of SEQ ID NO:1 and as shown in FIG. 1A. This glycosylated spacer polypeptide can extend out up to 80 angstroms from the surface of the membrane.

Figure 1B:
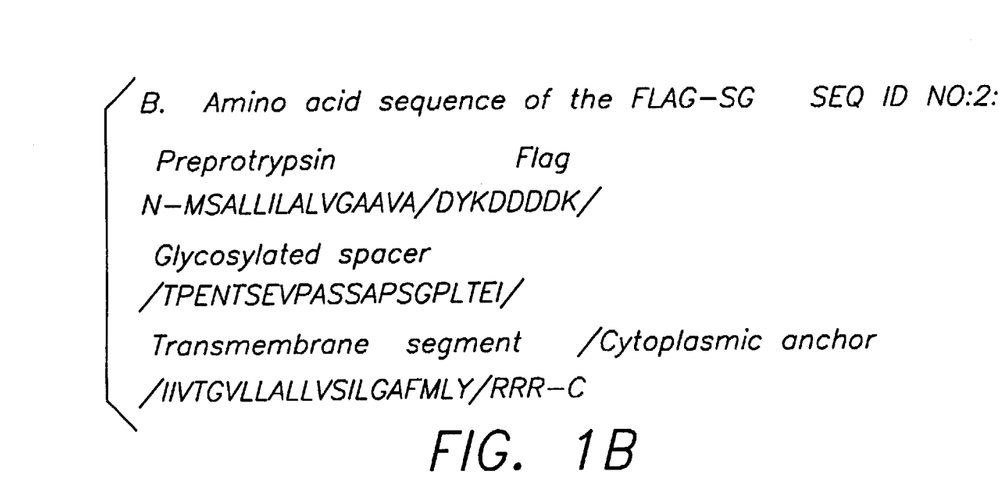
FIG. 1B shows the amino acid sequence encoded by the synthetic gene (SEQ ID NO:2).

The preferred embodiment of the synthetic gene of the present invention consists of the sequence of 204 nucleotides shown in SEQ ID NO:1 and in FIG. 1A. The synthetic gene sequence of FIG. 1A encodes the polypeptide consisting of the 68 amino acids shown in SEQ ID NO: 2 and in FIG. 1B.

Although it is not preferred, other segments can be added to the synthetic gene of this invention, such as segments encoding additional amino acids which will not interfere with the expression of the synthetic gene and the use of the gene to identify cells transfected with the synthetic gene.

The synthetic gene of this invention can be made by any method known in the art for synthesizing an entire synthetic gene in one step or synthesizing or otherwise assembling segments of nucleotides and then linking the segments of nucleotides together to form the synthetic gene in one or more steps. It is preferred that the deoxyribonucleotide or ribonucleotide sequence be designed where possible to use the most common codon for each amino acid for the particular cell into which it is inserted. Examples of methods of synthesizing the synthetic gene of this invention include polymerase chain reaction (PCR)-based gene assembly, or recombinant DNA or RNA techniques known to a person of ordinary skill in the art. The most preferred method of making the synthetic gene is by the method of PCR-based gene assembly which is a method disclosed and described in patents owned by Hoffman-LaRoche and is further described in Example 1 below. These patents include U.S. Pat. Nos. 5,219,727; 5,176,995; 4,683,202; 4,683,195; and 5,091,310, all incorporated herein by reference.

The present invention also provides the method of selecting cells comprising the steps of: inserting the synthetic gene into a sample of cells, said synthetic gene comprises a secretion leader segment, a cell marker segment and a transmembrane segment; allowing said sample of cells to express said synthetic gene; and using an affinity technique to identify the presence of the expressed synthetic gene.

Any known method can be used to insert the synthetic gene into a cell. It is preferred to use a transfection vector to insert the synthetic gene into a cell. The synthetic gene can be inserted into a transfection vector by any conventional recombinant DNA or RNA techniques. Many examples of useful recombinant DNA or RNA techniques which can be used for inserting the synthetic gene into the transfection vector include those disclosed and described in Sambrook, J. et al, *Molecular Cloning: A Laboratory Manual*, 2nd Ed., Cold Spring Harbor Laboratory Press (1989), incorporated herein by reference. Because it is preferred to insert the synthetic gene into a transfection vector, it is preferred to add restriction enzyme sites on each end of the synthetic gene when synthesizing the synthetic gene.

The transfection vector can be any vector that is compatible with the cell into which it is inserted. Transfection vectors preferably contain eukaryotic gene expression control elements such as transcriptional promoters and enhancers and translational control signals and enhancers, and introns and others which are known to person of ordinary skill in the art. The most preferred use of the synthetic gene of this invention is to select or identify mammalian cells; therefore, the preferred transfection vectors are compatible with mammalian cell types. Examples of useful transfection vectors are reviewed in Kaufman, *Methods in Enzymology*, Vol. 185, pg. 487, Academic Press (1990), incorporated herein by reference. Examples of the transfection vectors disclosed and described by Kaufman which are compatible with mammalian cells are listed in Table 1. The most preferred transfection vectors are shuttle vectors. Shuttle vectors are vectors which are capable of replication in both bacterial and mammalian cells.

TABLE 1

| Origin of Transfection vector | Examples of Cell Types With Which Transfection Vector is Compatible |
| --- | --- |
| Simian Virus 40 | Monkey and Human |
| Adenovirus | Monkey and Human |
| Bovine Papilloma Virus | Murine |
| Retrovirus | Murine |
| Vaccinia Virus | Primate and Rodent |
| Epstein Barr Virus | Primate and Rodent |
| Herpes Simplex Virus | Neurons |

The synthetic gene of this invention can be incorporated into transfection vectors designed for expression of multiple genes, preferably heterologous genes. In this application, the experimental gene of interest will be cloned into a multiple cloning region of the transfection vector that is bounded by appropriate eukaryotic gene expression control elements, and the synthetic gene of this invention will be inserted preferably by using restriction enzymes at another location within the transfection vector that is also bounded by appropriate eukaryotic gene expression control elements. Particularly useful transfection vectors for this application are designed with more than one multiple cloning region. Examples of useful transfection vectors with multiple cloning regions are described by Wang et al., *Gene*, Vol. 119, pg. 155(1992), incorporated herein by reference. After insertion of the transfection vectors containing the synthetic gene and the experimental gene of interest into the cell sample, the cells into which the transfection vectors were inserted can be identified using any known affinity techniques. Another method of inserting the synthetic gene and an experimental gene of interest into a transfection vector is disclosed by Levine, F. et al., *Gene*, Vol. 108, pp. 167-74 (December 1991), incorporated herein by reference.

The transfection vector with the synthetic gene inserted into it, is inserted into cells by methods such as calcium phosphate precipitation, electroporation and by the use of liposomes. Other methods are disclosed and described in Kriegler, M., *Gene Transfer and Expression a Laboratory Manual*, W. H. Freeman and Company, New York (1990), incorporated herein by reference. The preferred method is by electroporation of a sample of cells.

Once the cells have been transfected with the synthetic gene, they are usually placed in a compatible medium at a physiologically compatible temperature range for any where from between a few hours to a few days. This time period, temperature and medium are to encourage and allow the transfected cells to express the synthetic gene.

The preferred affinity techniques for the identity of the cells into which the synthetic gene has been inserted and which express the polypeptide surface marker are preferably affinity techniques which are specific to the polypeptide surface marker expressed by the synthetic gene. The affinity techniques often use molecules which possess a specific affinity for or bind to the polypeptide surface marker, including antibodies or other molecules such as proteins. Examples of types of antibodies useful in this invention include single chain antibodies, antibody fragments, genetically-engineered antibodies, polyclonal antibodies and monoclonal antibodies. Specific examples of molecules that can be used to identify various polypeptide surface markers include metal ions useful for the identification of cells expressing Histidine Sequence as a polypeptide surface marker; Glutathione useful for the identification of cells expressing Glutathione-S-Transferase as a polypeptide surface marker, (see Smith, D. B., and Johnson, K. S., *Gene*, Vol 67, pp. 31–40 (1988), incorporated herein by reference); and Maltose useful for the identification of cells expressing Maltose-Binding-Protein as a polypeptide surface marker.

Cells expressing the polypeptide surface marker which have been marked by the chosen primary antibodies or molecules can be separated from cells which do not express the polypeptide surface marker or otherwise were not marked by the primary antibodies or molecules. One example of a suitable affinity technique includes fluorescence activated cell sorting (FACS). In FACS, a secondary antibody which is tagged with a fluorescence material, such as fluorescein isothiocyanate (FITC), or rhodamine isothiocyanate (RITC), is introduced into a cell sample containing cells which have expressed the polypeptide surface marker and which are marked with a primary antibody. The primary antibody is attached to the polypeptide surface marker. The secondary antibody binds to the primary antibody. Cells having the secondary antibody will fluoresce and separation can be achieved by a fluorescence activated cell sorter. FACS can be used to separate cells expressing FLAG® polypeptide surface markers which are bound to a primary antibody specific to FLAG®, such as anti-FLAG® M1, M2 or M5, by using an appropriate anti-mouse IgG secondary antibody tagged with a fluorescent material, as disclosed and described in Kunz et al., *J. Biol. Chem.*, Vol. 267, pg. 9101 (1992), incorporated herein by reference. FLAG® and anti-FLAG® are registered trademarks of Immunology Ventures and are products which are commercially available from the Eastman Kodak Company.

Another affinity technique by which cells expressing the polypeptide surface marker may be identified from the remainder of a cell sample is through the use of antibodies or other molecules coupled to beads. The antibodies or other molecules coupled to the beads can bind directly to the polypeptide surface marker. Alternatively, the secondary antibodies or other molecules can be coupled to the beads, and the secondary antibodies or other molecules can be specific to the primary antibodies or molecules which bind to the polypeptide surface marker. A method of attaching antibodies to beads is disclosed and described in U.S. Pat. No. 5,011,912, incorporated herein by reference. For example, cells expressing the FLAG® polypeptide surface marker can be separated from cells which do not express FLAG® by using anti-FLAG® M1 and M2 monoclonal antibodies which are coupled to beads by means of a hydrazide linkage, which is described by Brizzard et al., *Biotechniques*, Vol. 16, pg. 730 (1994), incorporated herein by reference. To accomplish separation using this affinity separation technique, a sample of cells which have expressed the polypeptide surface marker and those which have not expressed the polypeptide surface marker are typically mixed with beads which are coupled to a primary antibody specific to the polypeptide surface marker. Cells which have expressed the polypeptide surface marker will bind to the antibodies coupled to the beads and the other cells will not. The cells bound to the beads can then be recovered by, for example, centrifugation.

Another affinity technique used to identify cells expressing the polypeptide surface marker is to couple a ligand, such as biotin, to antibodies or other molecules that have an affinity to the polypeptide surface marker or to primary antibodies or other molecules that bind to the polypeptide surface marker. For example, the anti-FLAG® monoclonal antibodies can be coupled to biotin by a hydrazide linkage, and the cells expressing the FLAG® polypeptide surface marker can then be separated from cells that do not express FLAG® through the use of avidin or streptavidin attached to magnetic beads. When the sample is placed in a magnetic field only the cells expressing FLAG® will bind to the magnetic beads via the linkage between the anti-FLAG antibody and the bonds between, for example, the biotin and avidin. The cells attached to the beads can be recovered and the others washed away.

In the preferred embodiment mammalian cells will be transfected with a synthetic gene encoding the FLAG® polypeptide surface marker. The transfected cell will express FLAG® at the cell surface. Anti-FLAG® murine monoclonal antibodies, for example, anti-FLAG® M1, M2 and M5 can be used to identify and select the cells expressing FLAG at the cell surface. Anti-FLAG-M1® is disclosed and described as antibody 4E11 in U.S. Pat. No 5,011,912, which was incorporated by reference above. Anti-FLAG-M1® has also been deposited at the American Type Culture Collection (ATCC), 12301 Parklawn Drive, Rockville, Md. 20852, pursuant to and in satisfaction of the requirements of the Budapest Treaty on the International Recognition of the Deposit of Microorganisms for the Purposes of Patent Procedure. The hybridoma designated 4E11 which produces the anti-FLAG-M1® antibody was deposited as ATCC Accession No. HB 9259 on Nov. 12, 1986. All restrictions imposed by the depositor on the availability to the public of the deposited biological material will be irrevocably removed upon the granting of the patent on the present application. The binding of the anti-FLAG-M1® monoclonal antibody to the FLAG® polypeptide surface marker is calcium-dependent. This is a significant feature, because after the identification of the transfected cells by anti-FLAG-M1®, the binding of the anti-FLAG-M1® antibody to the FLAG® polypeptide surface marker can be disrupted by the removal of calcium and the cells can be recovered minus the antibody for further use or study. The binding of the anti-FLAG M2® monoclonal antibody to the FLAG® polypeptide surface marker is not calcium-dependent; however, the binding of the anti-FLAG M2® monoclonal antibody can be disrupted by the addition of free FLAG® peptide. This method is described in, Brizzard et al., Biotechniques, Vol. 16, pg. 730 (1994), incorporated herein by reference. The anti-FLAG® monoclonal antibodies, therefore, offer a range of alternatives for the identification and selection of transfected cells which express FLAG®.

In addition to offering a means to select newly transfected cells in vitro, the disclosed invention may be used as a cell marker in vivo to follow the fate of cells within living organisms or to isolate pure population of cells of particular types from transgenic animals. This could be done by placing the synthetic gene under the control of a transgene with a promoter specific to the desired cell type, inserting the synthetic gene into an animal's cells to make a transgenic animal, then disaggregating the animal's tissues into free cell suspensions by enzyme treatment, for example with hyaluronidase and collagenase, and identifying the cells expressing the synthetic gene by the steps described above. By this method pure, non-tumerous, primary cell cultures can be made. The cells types to be isolated could be those that produce a valuable natural products, such as properly glycosylated tissue plasminogen.

The following examples further illustrate the invention. In the examples, the most common codons were used except where the method required otherwise.

EXAMPLE 1

Synthesis of a Synthetic Gene

Figure 2:
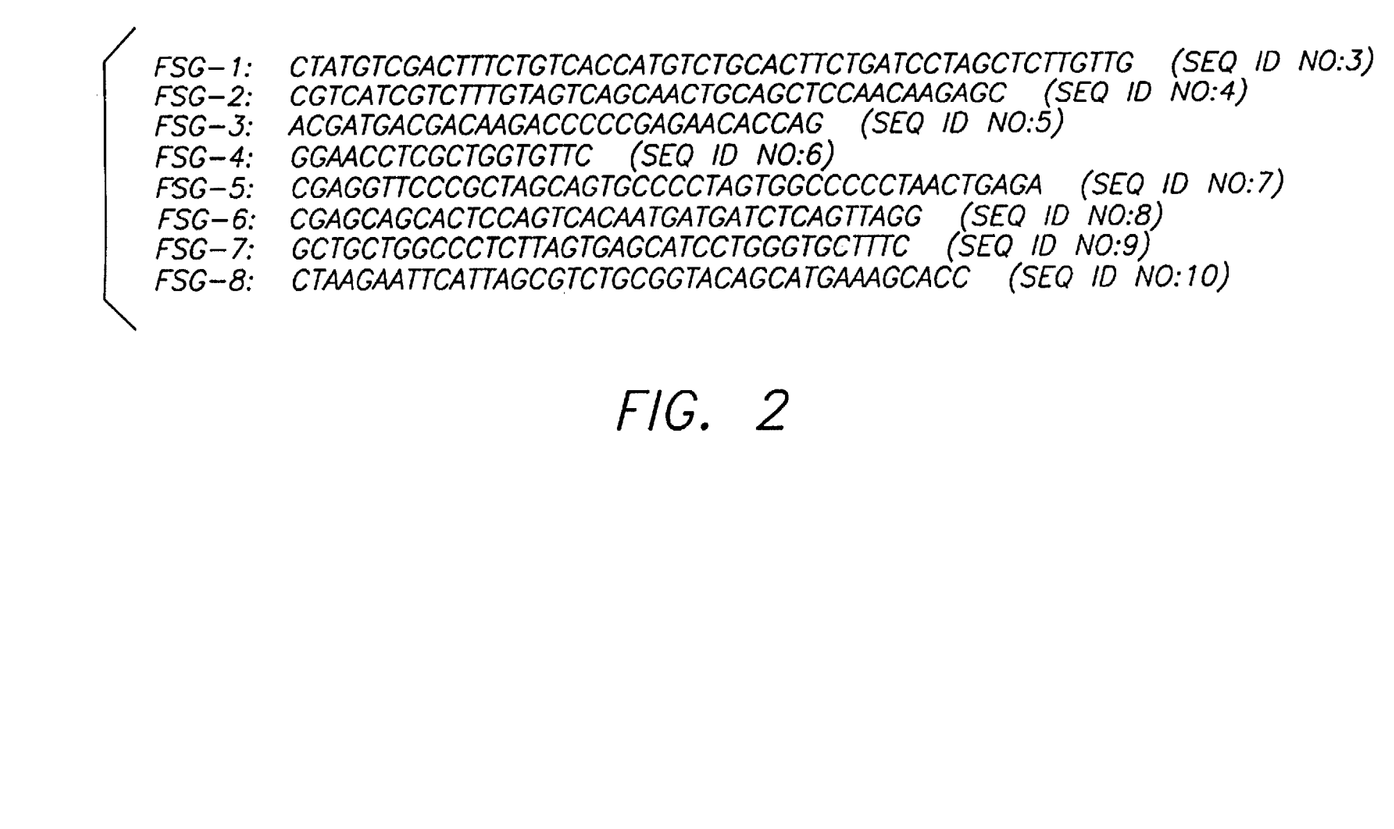
FIG. 2 shows the DNA sequence of 8 oligonucleotides used for the synthesis of the synthetic gene (SEQ ID NO:3 to SEQ ID NO:10).

Eight synthetic oligonucleotides shown in FIG. 2 (SEQ ID NO:3 to SEQ ID NO:10, inclusive) were used to construct the synthetic gene shown in FIG. 1A. The eight oligonucleotides were synthesized using the BioSearch 8600 DNA synthesizer, then purified over HPLC, and then phosphorylated. These oligonucleotides were mixed in equimolar amounts, heated for denaturation and then slow cooled to room temperature to anneal. To this mixture, Klenow fragment, supplied by IBI and T4 DNA ligase supplied by IBI were added to fill in and ligate. The sample was subjected to agarose gel electrophoresis. This process created a smear on an agarose gel. The region in the expected size range (240 base pairs) was excised and amplified by polymerase chain reaction (PCR) using FSG-1 (SEQ ID NO:3) and FSG-8 (SEQ ID NO:10) as primers. Again, the sample was subjected to agarose gel electrophoresis and the region of a smear on the agarose gel which corresponded to the 240 base pair size was excised and PCR amplified again. This was repeated two more times which resulted in a single band on an agarose gel. This DNA was cut with EcoRI and SalI both supplied by IBI, and ligated into the EcoRI/SalI cut pUC18 plasmid DNA supplied by IBI. Following transformation of E. coli, colonies were picked, and plasmid DNA was purified and sequenced for accuracy. A single colony construct was identified which had the desired DNA sequence. The synthetic gene produced encoded for the FLAG® polypeptide surface marker; therefore, it will be referred to as the FLAG® synthetic gene.

EXAMPLE 2

Cloning and Expression of the Synthetic Gene

Figure 3:
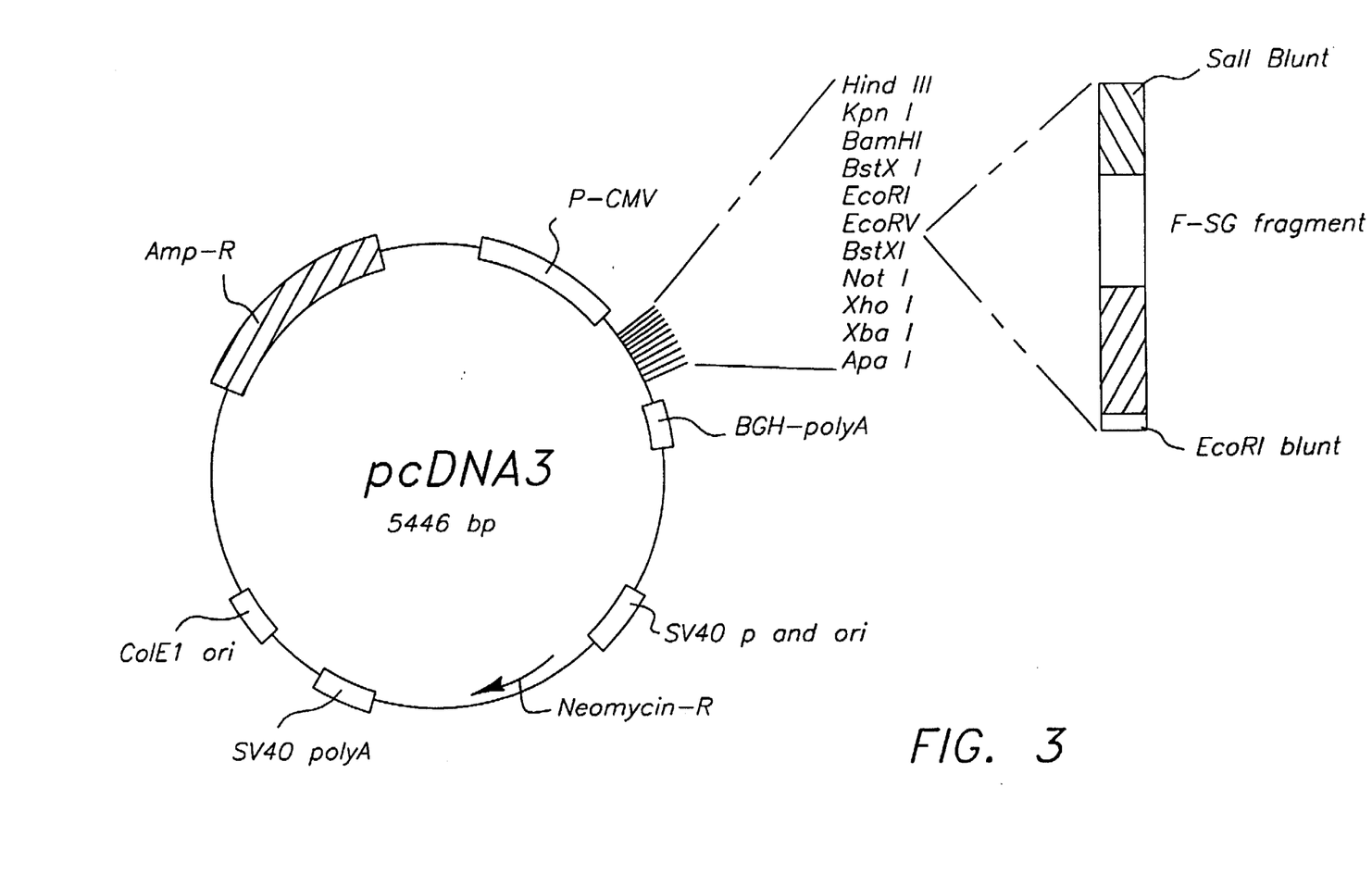
FIG. 3 shows the features of a mammalian transfection vector into which the synthetic gene is inserted.

The pUC18 plasmid containing the FLAG® synthetic gene made in Example 1 was EcoRI/SalI cut, filled in with Klenow and deoxyribonucleotide triphosphates, and purified from an agarose gel using the glass milk bead fragment purification procedure from Bio101, Inc. This blunt end fragment was inserted into the EcoRV site of the multiple cloning region of the mammalian transfection vector pcDNA3 supplied by Invitrogen, Inc. The FLAG® synthetic gene and the pcDNA3 transfection vector are shown in FIG. 3. As shown in FIG. 3, the multiple cloning region of pcDNA3 is flanked by the CMV promoter and the bovine growth hormone polyadenylation region. Other significant features of this vector include the colE1 origin and ampicillin resistance for propagation of the vector DNA in E. coli, as well as the SV 40 DNA replication origin and neomycin resistance gene for growth and selection of mammalian cells in media containing G418™ supplied by Life Technologies, Inc. The pcDNA3 construct containing the FLAG-synthetic gene was designated pCMF15.

Ten micrograms of pCMF15 was linearized with BglII and used to electroporate $5 \times 10^6$ cos-1 cells (from the American Type Culture Collection) at a field strength of 800 V/cm and a tau value of approximately 4.5 msec using an IBI Gene Zapper™ available from the Eastman Kodak Co. Cells were then plated in Dulbecco's Modified Eagle Medium (DMEM) supplemented with glutamine, and 10% Fetal Calf Serum (FCS) supplied by Life Technologies, Inc. After 48 hours, selection was started by the addition of 300 µg/mL of G418™ supplied by Life Technologies, Inc. Selection was maintained for another seven days and the remaining viable cells were immunologically stained. The staining protocol consisted of first fixing the cells to the tissue culture dish with 4 percent formaldehyde/tris buffer saline (TBS) in 1 mM $CaCl_2$. Fixed cells were blocked with 5 percent FCS for 1 hour at 37° C. and incubated for 20 minutes in 3 percent hydrogen peroxide to remove residual peroxidase activity. They were then washed with TBS in 1 mM $CaCl_2$, incubated 30 minutes with Biotinylated-M2, washed again, and incubated for thirty minutes with Avidin-Biotin Complex (ABC) supplied by Vector Laboratories. Biotinylated-M2 is a biotinylated primary antibody, specifically it is biotinylated-anti-FLAG-M2® antibody which is specific to the FLAG® polypeptide surface marker. Biotin was covalently attached to the anti-FLAG M2® antibody using Biotin-LC-hydrazide from Pierce, Inc. according to the manufacturer's instructions. (The method of attaching Biotin to an antibody is further disclosed and described in O'Shannessy, D. J. et al Immunol. Lett., Vol. 8, pg 273–277 (1984), incorporated herein by reference. O-dianisidine supplied by Sigma, Inc. was used for colorimetric detection of the binding of the biotinylated antibody to the polypeptide surface marker. Under light microscopy, areas of reddish-brown staining were present. The staining identified cells that were transfected with the pCMF15, which expressed the FLAG® polypeptide surface marker and to which the Biotinylated-M2 bonded.

COMPARATIVE EXAMPLE 1

Ten micrograms of pcDNA3 that was not transfected with the synthetic gene of Example 1, was linearized with BglII and used to electroporate $5\times10^6$ cos-1 cells (from the American Type Culture Collection). These cells were prepared and analyzed the same as cells transfected with the pCMF15 as described in Example 2. Under the same magnification as described in Example 2, none of the pcDNA3 indicated a reddish-brown stain.

EXAMPLE 3

Selection of Transfected Cells

CHO-K1 cells supplied by the American Type Culture Collection were grown in suspension in CHO-SFM supplied by Life Technologies, Inc. to a population of approximately 25 million cells per T75 flask. The cells were pelleted, washed two times with one half volume of phosphate buffered saline, pH 7.4 (PBS). The cells were again pelleted and resuspended in one tenth volume of PBS to a final concentration of 10 million cells/mL. The cells were transfected by electroporation with 10 micrograms of linearized pCMF15 made as described in Example 2. 0.8 mL (8 million cells) were incubated at room temperature with pCMF15 for fifteen minutes, and electroporated at 850 V/cm and a tau value of approximately 5 msec. These cells were added to 15 volumes of Ham's F-12™ medium supplied by Life Technologies, Inc., subdivided into 2 mL aliquots in 9 $cm^2$ tissue culture dishes and placed in an incubator at 37° C. and 5% $CO_2$. After 24 hrs. growth, the cells were washed with Hank's Balanced Salt™ solution supplied by Life Technologies, Inc., and 2 mL of selective media (Ham's F-12 and 200 µg/mL G418™ supplied by Life Technologies, Inc.) was added. Cells were maintained in this media for six weeks until large, discreet colonies were visible on the plates.

Two plates having the colonies of cells were tested for growth with M1 Affinity Gel Beads available from Eastman Kodak. The M1 Affinity Gel Beads are beads having anti-FLAG-M1® Antibody coupled to them. The M1 Affinity Gel Beads were washed 4 times with growth medium (Ham's F-12™ which contains calcium chloride for M1 attachment), and 100 µL of the beads were added to each of the two plates of CHO-K1 cells transfected with pCMF15. These plates were incubated overnight at 37° C. and 5% $CO_2$ and observed by light microscopy.

The cells incubated with the M1 Affinity Gel Beads showed significant clumping and binding to the beads.

COMPARATIVE EXAMPLE 2

Two additional plates prepared as in Example 3 having the same colonies of CHO-K1 transfected with pCMF15 were tested for growth with affinity gel beads supplied by Unisign, Inc. These affinity gel beads were not coupled to the anti-FLAG-M1® Antibody. The beads and plates were prepared and observed by light miscroscopy as those described in Example 3. The cells were not clumped and bound to the uncoupled affinity gel beads like the cells grown with the M1 Affinity Gel Beads of Example 3. The cells were bound to the beads as much as they were bound to the plate indicating no specific bonding of a polypeptide surface marker to the beads.

This invention has been described with reference to specific examples and particular embodiments, but it will be apparent to one of ordinary skill in the art that modifications can be made to the invention without departing from the spirit or scope of the claims.

---

We claim:

1. A synthetic gene comprising a secretion leader segment, a non-naturally occurring synthetic cell marker segment and a transmembrane segment.

2. The synthetic gene of claim 1 further comprising a spacer segment between said synthetic cell marker segment and said transmembrane segment.

3. The synthetic gene of claim 1 wherein said synthetic cell marker segment encodes a polypeptide surface marker.

4. A transfection vector comprising the synthetic gene of claim 1.

5. A cell comprising the transfection vector of claim 4.

6. A cell comprising the synthetic gene of claim 1.

7. A synthetic gene comprising a secretion leader segment, a non-naturally occurring synthetic cell marker segment, a transmembrane segment and an anchor segment after said transmembrane segment.

8. The synthetic gene of claim 3 further comprising a spacer segment between said synthetic cell marker segment and said transmembrane segment, and an anchor segment after said transmembrane segment.

9. The synthetic gene of claim 8 wherein said spacer segment comprises nucleotides 70 through 132 of SEQ ID NO:1, said transmembrane segment comprises nucleotides 133 through 195 of SEQ ID NO:1, and said anchor segment comprises nucleotides 196 through 204 of SEQ ID NO:1.

10. The synthetic gene of claim 3 wherein said synthetic cell marker segment encodes a polypeptide surface marker comprising both hydrophilic and aromatic amino acids and including the sequence of amino acid residue numbers 16–18 of SEQ ID NO:2.

11. A synthetic gene comprising a secretion leader segment, a non-naturally occurring synthetic cell marker segment and a transmembrane segment, wherein said synthetic cell marker segment encodes a polypeptide surface marker consisting of the sequence of amino acid residue members 16–23 of SEQ ID NO:2.

12. A synthetic gene comprising a secretion leader segment, a non-naturally occurring synthetic cell marker segment and a transmembrane segment, wherein said synthetic cell marker segment encodes a polypeptide surface marker to which a monoclonal antibody produced by the murine hybridoma designated 4E11 (ATCC HB 9259) will bind.

* * * * *